United States Patent
Badalemente et al.

(10) Patent No.: US 7,854,929 B2
(45) Date of Patent: Dec. 21, 2010

(54) METHOD FOR TREATING LATERAL EPICONDYLITIS USING COLLAGENASE

(75) Inventors: Marie A. Badalemente, Mt. Sinai, NY (US); Edward Wang, Pozuott, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 12/115,256

(22) Filed: May 5, 2008

(65) Prior Publication Data

US 2009/0010918 A1 Jan. 8, 2009

Related U.S. Application Data

(63) Continuation-in-part of application No. 11/703,269, filed on Feb. 7, 2007, and a continuation-in-part of application No. 11/335,157, filed on Jan. 19, 2006, now abandoned.

(60) Provisional application No. 60/927,437, filed on May 3, 2007, provisional application No. 60/934,045, filed on Jun. 11, 2007, provisional application No. 60/934,046, filed on Jun. 11, 2007, provisional application No. 60/645,772, filed on Jan. 21, 2005, provisional application No. 60/677,440, filed on May 3, 2005, provisional application No. 60/719,470, filed on Sep. 22, 2005.

(51) Int. Cl.
*A61K 38/48* (2006.01)
(52) U.S. Cl. ......................... 424/94.67; 435/7.1; 514/12
(58) Field of Classification Search ........................ None
See application file for complete search history.

(56) References Cited

U.S. PATENT DOCUMENTS

| 4,524,065 A | 6/1985 | Pinnell et al. |
| 4,645,668 A | 2/1987 | Pinnell et al. |
| 6,335,388 B1 | 1/2002 | Fotinos et al. |
| 6,358,539 B1 | 3/2002 | Murad et al. |

OTHER PUBLICATIONS

Galardy et al..(Biochemistry, vol. 22, pp. 4556-4561, 1983).*
Jung et al. ( J. of Bacteriology, vol. 181, No. 9, pp. 2816-2822, 1999).*
Badalamente, Marie A., et al. "Efficacy and Safety of Injectabel Mixed Collagenase Subtypes in the Treatment of Dupuytren's Contracture," The J. of Hand Surgery, 32A(6):767-774 (2007).
Health News, WebMD, pp. 1-2 (2006).
SurgerNews.Net, pp. 1-3, Apr. 2005.
Rotunda, Adam, M. et al., "Mesotherapy and phosphatidycholine injections: historical clarification and review," Dematologic Surgery: Official Publication for American Society for Dermatologic Surgery [et al.] 32(4):465-480 (2006).

* cited by examiner

*Primary Examiner*—Hope A Robinson
(74) *Attorney, Agent, or Firm*—Elmore Patent Law Group, P.C.; Carolyn S. Elmore; Mahreen Chaudhry Hoda

(57) ABSTRACT

Methods for treatment by collagenase injections are provided, which are effective in dissolving and lysing a collagenase septa network to treat carpal tunnel, plantar fasciitis and lateral epicondylitis conditions. The methods treat such conditions by injecting or otherwise delivering purified collagenase to the afflicted region of the patient, as well as use of collagenase for manufacture of a medicament for such conditions.

6 Claims, No Drawings

METHOD FOR TREATING LATERAL EPICONDYLITIS USING COLLAGENASE

PRIORITY

This application claims priority to U.S. Provisional Application No. 60/927,437, filed May 3, 2007, to U.S. Provisional Application No. 60/934,045, filed Jun. 11, 2007, to U.S. Provisional Application No. 60/934,046, filed Jun. 11, 2007, to U.S. Provisional Application No. 60/645,772 filed on Jan. 21, 2005, to U.S. Provisional Application No. 60/677,440 filed on May 3, 2005 and U.S. Provisional Application No. 60/719,470 filed on Sep. 22, 2005, and is a continuation in part of U.S. application Ser. No. 11/703,269, filed with the U.S. Patent and Trademark Office on Feb. 7, 2007, and is a continuation in part of U.S. application Ser. No. 11/335,157, filed with the U.S. Patent and Trademark Office on Jan. 19, 2006, the contents of each of which is incorporated herein by reference.

GOVERNMENT SUPPORT

The invention was supported, in part, by a grant M01RR10710 from the National Institutes of Health. The U.S. Government may have certain rights in the invention.

BACKGROUND OF THE INVENTION

Numbness of the fingers and parasthesia are common symptoms of Carpal Tunnel Syndrome ("CTS"). A stressed-median nerve coupled with increased compression accompanying bending of the wrist creates numbness and tingling. CTS can result in difficulty gripping and making a fist, and dropping objects. Conventional remedies for CTS include non-steroidal anti-inflammatory mediations, splinting at night and sometimes corticosteroid injection of the carpal canal. CTS can also treated surgically, either endoscopically or by open surgery. In contrast to the invasive and disruptive conventional treatments of CTS, the present invention treats CTS by collagenase injection directed at the transverse carpal ligament.

Micro tearing of the origin of the plantar fascia at the medical calcaneal tuberosity can often lead to inflammation and fibrosis of collagen tissue. The plantar fascia is the membrane beneath the skin on the bottom of the foot that helps anchor the skin to deeper structures of the foot. Plantar fasciitis is a very common cause of heel pain, usually occurring in middle age and typically not related to trauma. Current treatment modalities are limited to physical therapy, cortisone shots and surgery. Physical therapy is usually prolonged and therefore can become very expensive. Cortisone shots frequently have to be repeated and are very painful. Typically, plantar fasciitis causes months of pain before relief is achieved. Surgery to cut the attachment of the plantar fascia from its origin on the calcaneus is used in cases that do not respond to conservative treatment. However, complications with surgery include damage to nerves in the sole of the foot. The present invention provides a simple non-surgical solution for plantar fasciitis by the use of collagenase injection, directed at the damaged, fibrotic, collagen tissue.

Lateral epicondylitis, also known as tennis elbow, is a very common cause of impairment and pain in the arm. Lateral epicondylitis results from tearing of the origin of the extensor muscles from the elbow. Such tears are usually partial and are slow to heal. A repetitive traumatic injury at the extensor origin heals through fibrosis of collagen tissue. Current treatments include cortisone shots, physical therapy and bracing, which work in most cases. However, a significant number of people have a prolonged course of treatment. This becomes expensive. Surgery is the last option used when conservative treatment fails. Surgery is used to remove the damaged tissue, including fibrotic collagen tissue, at the bone.

To date there remains a need for an effective treatment of carpal tunnel, plantar fasciitis and lateral epicondylitis conditions. It is the object of invention to provide such methods of treatment.

SUMMARY OF THE INVENTION

The present invention relates to the discovery that collagenase injections are effective in providing purified collagenase to collagenous adhesions of a finger and other joints and afflicted areas to provide a method for non-surgical treatment of CTS, of collagenous elbow and/or knee joint adhesions, and to dissolve fibrous adhesions in a sole of a patient's foot to non-surgically treat plantar fasciitis.

In a preferred embodiment, fibrous adhesions are dissolved by use of Clostridiopeptidase A derived from bacterium *Clostridium hisolyticum*, which is preferably administered in an absence of triamcinolone or other corticosteroids.

DETAILED DESCRIPTION OF THE PREFERRED EMBODIMENTS

The present invention is related to the discovery of the effectiveness of collagenase injections. That is, the present invention relates to treating a patient by injecting an effective amount of collagenase to affected regions of carpal tunnel, plantar fasciitis and lateral epicondylitis conditions. The present invention also relates to the use of collagenase in the manufacture of a medicament to treat carpal tunnel, plantar fasciitis and lateral epicondylitis conditions.

As described in U.S. patent application Ser. Nos. 11/335,157 and 11/703,269, collagenase treatment has proven effective for treatment of adhesive capsulitis, also known as frozen shoulder, and for reduction of cellulite. Collagenase injections have been proposed for the treatment of diseases such as Dupuytren's disease, adhesive capsulitis and Peyronie's disease, associated with collagen cords or plaques. See, U.S. Pat. Nos. 5,589,171, 6,086,872, 6,022,539, of Wegman, which are incorporated herein by reference.

The published work of the inventor, Dr. Badalamente, in Dupuytren's disease forms the rationale for the present invention (Starkweather, K., Lattuga, S., Hurst, L. C., Badalamente, M. A., Guilak, F., Sampson, S. P., Dowd, A., Wisch, D. *Collagenase in the Treatment of Dupuytren's Disease: An in vitro Study*, J. Hand Surg. 21A:490-95, 1996; Badalamente, M. A., Hurst, L. C., *Enzyme Injection as a Non-operative Treatment for Dupuytren's Disease*, J. Drug-Delivery 3(1): 35-40, 1996; Hurst, L. C., Badalamente, M. A. (invited authorship) *Non-operative Treatment of Dupuytren's Disease*, Hand Clinics, G. M. Rayan (ed). W.B. Saunders 15(1), 97-107, 1999; Hurst, L. C., Badalamente, M. A. (invited editors & authorship), *Dupuytren's Disease*, R. Tubinana, R. Tubiana, C. Leclercq, L. C. Hurst, M. A. Badalamente (eds), Martin Dunitz Publisher, London (2000); Badalamente, M. A., Hurst, L. C. *Enzyme Injection as a Non-operative Treatment of Dupuytren's Disease*, J. Hands Surg. 25A(4); 629-36, 2000; Badalamente, M. A., Hurst, L. C., Hentz, V. R. *Collagen as a Clinical Target: Non-operative Treatment of Dupuytren's Disease*, J. Hand Surg. 27A(5):788-98, 2002, Badalamente, M. A., Hurst, L. C. *Efficacy and Safety of Injectable Mixed Collagenase Subtypes in the Treatment of Dupuytren's Contracture*, J. Hand. Surg. 32A(6): 767-774, 2007). In Dupuytren's disease, the pathognomonic fibrous cord is often interspersed with a septa-like arrangement of adipose tissue. These present clinically as mattress-type "lumps" of varying sizes, and in Dupuytren's disease, are termed nodules. It has been a consistent clinical finding in both Phase 2 and 3 trials for Dupuytren's disease that after purified Clostridial collagenase injection, not only does the collagenous cord dissolve and rupture when subjected to pressure in extension, but the fibro-fatty nodules also resolve, and harmlessly resorb. Therefore, collagenase injected subcutaneously into afflicted areas was postulated to be a safe and effective treatment.

Collagenase is an enzyme that has specific ability to digest collagen. A preferred form of a collagenase is derived from fermentation by *Clostridium hisolyticum* and is purified by a chromatographic technique, such as that disclosed in U.S. Provisional Application Ser. No. 60/763,470 filed on Jan. 20, 2006, which is incorporated herein by reference. Collagenase naturally produced by *Clostridium hisolyticum* once purified will exhibit two distinct peaks when run on an electrophoresis SDS gel. It is these two distinct peaks that are referred to as collagenase I and collagenase II.

Sterilized lyophilized collagenase powder is commercially available having a minimum assay of 50 units per mg. The assay may range considerably above that from batch to batch, but is taken into account in determining the weight of the powder to use with a pharmaceutically acceptable carrier, for example, normal saline, in preparing a desired concentration for treatment.

The collagenase is applied in a liquid carrier that is pharmaceutically acceptable, including inertness towards the collagenase. Examples are normal saline, aqueous NaCl/CaCl$_2$ buffer, aqueous dextran solution, and aqueous hetastarch solution.

One form of purified collagenase used for injection is comprised of two microbial collagenases, referred to as "Collagenase ABC I" and "Collagenase ABC II". Both collagenases are isolated and purified from the fermentation of the bacterium *Clostridium hisolyticum* and belong to the same metalloprotease.

Collagenase ABC I is a single polypeptide chain consisting of approximately 1000 amino acids of known sequence. It has an observed molecular weight of 115 kiloDalton (kD), an isoelectric point (pI) between 5.63-5.68 and an extinction coefficient of 1.480. From its activity behavior toward synthetic substrate, it has been determined that Collagenase ABC I is the class I *Clostridium hisolyticum* collagenase in the literature.

Collagenase ABC II is also a single polypeptide chain consisting of about 1000 amino acids of deduced sequence. It has an observed molecular weight of 110 kD, an isoelectric point between 5.46-5.57 and an extinction coefficient of 1.576. Collagenase ABC II functionally belongs to the class II *Clostridium hisolyticum* collagenase in the literature.

The drug substance may have a 1 to 1 mass ratio for collagenase ABC I and ABC II with an extinction coefficient of 1.528. Both collagenases require tightly bound zinc and loosely bound calcium for their activity. Collagenase ABC I and Collagenase ABC II are not immunologically crossreactive and have a very broad hydrolyzing reactivity toward all types of collagen. Even though each collagenase shows different specificity, together they show synergistic activity toward collagen.

Lyophilized collagen for injection is purified clostridial collagenase prepared as a lyophilized formulation and may contain about 0.1 mg lactose monohydrate USP per 1,000 ABC units of collagenase activity.

A preferred collagenase composition comprises a mixture of collagenase I and collagenase II in a mass ratio of about 1 to 1 and having specific activity from about 500 SRC units/mg to about 15,000 SRC units/mg, preferably of at least about 700 SRC units/mg, more preferably of at least about 1000 SRC units/mg, even more preferably at least about 1500 SRC units/mg. One SRC unit will solubilize rat tail collagen into ninhydrin reaction material equivalent to 1 nanomole of leucine per minute, at 25 degrees C., pH 7.4. Collagenase has been described in ABC units as well, with 10,000 ABC of approximately 0.58 mg. The potency assay of collagenase is based on the digestion of undenatured collagen (from bovine tendon) at pH 7.2 and 37 degrees C. for 20-24 hours. The number of peptide bonds cleaved are measured by reaction with ninhydrin. Amino groups released by a solubilized digestion control are subtracted. One net ABC unit of collagenase will solubilize ninhydrin reactive material equivalent to 1.09 nanomoles of leucine per minute. One SRC unit equals approximately 6.3 ABC units.

Collagenase administration in the present invention is preferably via injection in a pharmaceutically acceptable liquid carrier. Preferably, the carrier does not interact or deactivate the collagenase. Examples are normal saline and aqueous NaCl/CaCl$_2$ buffer (containing 0.9% NaC$_l$ and 2 mM CaCl$_2$).

Treatment of CTS using the present invention is a non-surgical procedure in which collagenase injection is directed at a transverse carpal ligament. In other preferred embodiments, the collagenase injection is provided to the elbow and knee joint to treat post-traumatic elbow stiffness/lateral epicondylitis and knee stiffness, respectively. In the elbow the injection is preferably directed at the point of maximal tenderness, including the region of the insertion of the extensor carpi radialis brevis muscle. In the knee, the injection is preferably directed at the point of maximal tenderness, dependent on the site (anterior or posterior) of the knee joint contracture.

In an alternative preferred embodiment, fibrous adhesions in the sole of the foot are dissolved by collagenase injection directed at the damaged, fibrotic, collagen tissue, to provide a non-surgical solution for plantar fasciitis. In the foot, the injection is preferably directed at either the proximal plantar fascia for heel pain fasciitis or the distal plantar fascia in the mid foot for distal fasciitis. Advantages of the present inventive technology are that it is minimally invasive, does not require any extended rehabilitation and/or surgery and would return patients to normal activities or daily living.

Side effects of collagenase injection for plantar fasciitis may include edema and ecchymosis, as identified in studies in the hand (Dupuytren's disease) and frozen shoulder (Adhesive capsulitis). However, the present invention clearly shows that these effects are mild to moderate and resolve in one-two weeks.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A method of treating lateral epicondylitis in a patient in need thereof comprising administering an effective amount of purified collagenase I and II to an elbow joint of said patient, wherein the collagenase I and II are obtained from *Clostridium histolyticum* and wherein the effective amount is a dose comprising at least 1500 SRC units.

2. The method of claim 1, wherein the purified collagenase I and II are administered by injection.

3. The method of claim 1, wherein the purified collagenase I and II are injected in one or more injections in a dose comprising at least 1500 SRC units.

4. The method of claim 1, wherein the purified collagenase I and II are injected in a volume of about 1.0 ml.

5. The method of claim 1, wherein the treatment is repeated after about four to six weeks.

6. The method of claim 1, wherein the purified collagenase I and II are in a dose comprising approximately 10,000 ABC units, applied in one or more injections.

* * * * *

UNITED STATES PATENT AND TRADEMARK OFFICE
CERTIFICATE OF CORRECTION

PATENT NO.         : 7,854,929 B2                                                Page 1 of 1
APPLICATION NO.    : 12/115256
DATED              : December 21, 2010
INVENTOR(S)        : Marie A. Badalemente et al.

It is certified that error appears in the above-identified patent and that said Letters Patent is hereby corrected as shown below:

In Column 1, under GOVERNMENT SUPPORT lines 23-25, please delete "The invention was supported, in part, by a grant M01RR10710 from the National Institutes of Health. The U.S. Government may have certain rights in the invention" and insert -- This invention was made with government support under grant number RR010710 awarded by the National Institute of Health. The government has certain rights in the invention --.

Signed and Sealed this
Twenty-ninth Day of March, 2011

David J. Kappos
*Director of the United States Patent and Trademark Office*